(12) United States Patent
Konstandopoulos et al.

(10) Patent No.: US 8,261,540 B2
(45) Date of Patent: Sep. 11, 2012

(54) PARTICULATE MATTER SENSOR AND EXHAUST GAS PURIFICATION APPARATUS

(75) Inventors: Athanasios G. Konstandopoulos, Thessaloniki (GR); Fumishige Miyata, Ibi-Gun (JP); Senji Hamanaka, Ibi-Gun (JP); Takashi Yamakawa, Ibi-Gun (JP); Makoto Konno, Ibi-Gun (JP)

(73) Assignees: Ibiden Co., Ltd., Ogaki-Shi (JP); Athanasios G. Konstandopoulos, Thessaloniki (GR)

( * ) Notice: Subject to any disclaimer, the term of this patent is extended or adjusted under 35 U.S.C. 154(b) by 335 days.

(21) Appl. No.: 12/788,253

(22) Filed: May 26, 2010

(65) Prior Publication Data

US 2011/0072789 A1 Mar. 31, 2011

(30) Foreign Application Priority Data

Sep. 25, 2009 (WO) .................. PCT/JP2009/066689

(51) Int. Cl.
*F01N 3/031* (2006.01)

(52) U.S. Cl. ................. 60/297; 60/277; 60/286; 60/288; 60/295; 60/300; 60/303; 60/311; 55/282.2; 55/282.3; 55/283; 55/350.1; 96/421

(58) Field of Classification Search .................... 60/276, 60/277, 286, 288, 291, 295, 297, 300, 303, 60/311; 55/282.2, 282.3, 283, 350.1, 523; 95/8, 19; 96/417, 421
See application file for complete search history.

(56) References Cited

U.S. PATENT DOCUMENTS

| | | | | |
|---|---|---|---|---|
| 3,910,040 A * | 10/1975 | Garcea | | 60/277 |
| 4,538,411 A * | 9/1985 | Wade et al. | | 60/274 |
| 4,633,706 A | 1/1987 | Ito et al. | | |
| 4,685,066 A | 8/1987 | Hafele et al. | | |
| 4,887,427 A | 12/1989 | Shinzawa et al. | | |
| 5,239,861 A | 8/1993 | Fujita et al. | | |
| 5,489,319 A * | 2/1996 | Tokuda et al. | | 96/400 |
| 2007/0289293 A1 | 12/2007 | Kerchner et al. | | |
| 2007/0294999 A1* | 12/2007 | Yoshizaki et al. | | 60/274 |
| 2008/0120968 A1* | 5/2008 | Beall et al. | | 60/295 |
| 2009/0007546 A1* | 1/2009 | Ueda et al. | | 60/286 |
| 2009/0084097 A1* | 4/2009 | Sato et al. | | 60/311 |
| 2010/0005786 A1* | 1/2010 | Hinz et al. | | 60/286 |
| 2011/0036080 A1* | 2/2011 | Beall et al. | | 60/299 |

FOREIGN PATENT DOCUMENTS

EP 1916394 4/2008

(Continued)

Primary Examiner — Kenneth Bomberg
Assistant Examiner — Jorge Leon, Jr.
(74) Attorney, Agent, or Firm — Ditthavong Mori & Steiner, P.C.

(57) ABSTRACT

A particulate matter sensor includes a first detection filter provided in an exhaust gas flow passage and capable of collecting particle matter. A second detection filter is provided on a downstream side of the first detection filter in the exhaust gas flow passage and capable of collecting the particle matter. A first differential pressure detection unit is configured to detect a first differential pressure between pressures of an upstream side and the downstream side of the first detection filter. A second differential pressure detection unit is configured to detect a second differential pressure between pressures of an upstream side and a downstream side of the second detection filter. A particle matter amount detection unit is configured to detect an amount of particle matter based on a detection result of the first differential pressure detection unit and a detection result of the second differential pressure detection unit.

21 Claims, 5 Drawing Sheets

FOREIGN PATENT DOCUMENTS

| | | |
|---|---|---|
| JP | 60-242341 | 12/1985 |
| JP | 61-500864 | 5/1986 |
| JP | 2006-226808 | 8/2006 |
| JP | 2008-101602 | 5/2008 |
| JP | 2008-190470 | 8/2008 |
| WO | 98/32001 | 7/1998 |

* cited by examiner

PARTICULATE MATTER SENSOR AND EXHAUST GAS PURIFICATION APPARATUS

CROSS-REFERENCE TO RELATED APPLICATIONS

The present application claims priority under 35 U.S.C §119 to International Application No. PCT/JP2009/066689, filed Sep. 25, 2009, the entire contents of which are hereby incorporated herein by reference.

BACKGROUND OF THE INVENTION

1. Field of the Invention

The present invention relates to a particulate matter sensor and an exhaust gas purification apparatus.

2. Description of the Related Art

Conventionally, there is provided an exhaust gas purification apparatus, an exhaust gas purification method, and a particulate matter (PM) measuring method using a Diesel Particulate Filter (DPF) made of a porous ceramic material capable of collecting (removing) Particulate Matter (PM) including Carbon (C) as a main component of the Particulate Matter (PM) exhausted from a diesel engine. (Conventionally, there have been known an exhaust gas purification apparatus, an exhaust gas purification method, and a Particulate Matter (PM) measurement method) (see, for example, Japanese Patent Application Publication No.: 2008-101602A). In the exhaust gas purification apparatus, the Particulate Matter (PM) is gradually accumulated in the Diesel Particulate Filter (DPF) during continual use and the Diesel Particulate Filter (DPF) is periodically regenerated by burning and oxidizing the Particulate Matter (PM) in the Diesel Particulate Filter (DPF) to remove the Particulate Matter (PM). By regenerating the Diesel Particulate Filter (DPF), it becomes possible to prevent a clogging problem due to the accumulated Particulate Matter (PM) and continuous use of the Diesel Particulate Filter (DPF).

However, if the regeneration is performed when Particulate Matter (PM) is not so much accumulated, Particulate Matter (PM) may not be efficiently removed; namely, energy required for regenerating the Diesel Particulate Filter (DPF) may be wastefully consumed. On the contrary, if the regeneration is performed when there is too much Particulate Matter (PM) accumulated, an extra pressure loss may be generated between the upstream side and the downstream side of the Diesel Particulate Filter (DPF) in the exhaust gas flow passage in proportion to the delay in performing the regeneration process may increase the fuel consumption of the internal combustion engine. Therefore, to avoid this problem, it is thought to be required to always oxidize and remove the Particulate Matter (PM) in the Diesel Particulate Filter (DPF) (i.e., regenerate the Diesel Particulate Filter (DPF)) when an amount of particulate matter accumulated in the Diesel Particulate Filter (DPF) reaches a predetermined value (amount).

As a method of optimizing the timing for regenerating the Diesel Particulate Filter (DPF), there may be provided a measuring apparatus capable of measuring Particulate Matter (PM) accumulated in the Diesel Particulate Filter (DPF) by obtaining an amount of Particulate Matter (PM) accumulated in a detection filter provided in a secondary exhaust pipe bypassing a main exhaust pipe in which the Diesel Particulate Filter (DPF) is provided, the secondary exhaust pipe collecting a part of exhaust gas exhausted from the internal combustion engine as sample gas, where the amount of Particulate Matter (PM) accumulated in a detection filter is obtained based on a differential pressure between the upstream side and the downstream side of the detection filter.

In this measuring apparatus, the differential pressure is measured between the upstream side and the downstream side of the detection filter provided in the secondary exhaust pipe, and based on the measured differential pressure, the amount of the Particulate Matter (PM) accumulated in the detection filter is obtained (calculated). Then, based on the amount of the Particulate Matter (PM) accumulated in the detection filter, the amount of Particulate Matter (PM) accumulated in the Diesel Particulate Filter (DPF) is calculated. As a result, when determining that the amount of Particulate Matter (PM) accumulated in the Diesel Particulate Filter (DPF) exceeds a predetermined value, the regeneration of the Diesel Particulate Filter (DPF) is started. The entire contents of Japanese Patent Application Publication No. 2008-101602A, are hereby incorporated herein by reference.

SUMMARY OF THE INVENTION

According to a first aspect of the present invention, a particle matter sensor includes a first detection filter, a second detection filter, a first differential pressure detection unit, a second differential pressure detection unit, and a particle matter amount detection unit. The first detection filter is provided in an exhaust gas flow passage and capable of collecting particle matter. The second detection filter is provided on a downstream side of the first detection filter in the exhaust gas flow passage and capable of collecting the particulate matter. The first differential pressure detection unit is configured to detect a first differential pressure between pressures of an upstream side and the downstream side of the first detection filter. The second differential pressure detection unit is configured to detect a second differential pressure between pressures of an upstream side and a downstream side of the second detection filter. The particle matter detection unit is configured to detect an amount of particle matter based on a detection result of the first differential pressure detection unit and a detection result of the second differential pressure detection unit.

According to a second aspect of the present invention, an exhaust gas purification apparatus includes a diesel particulate filter, the particulate matter sensor according to the first aspect of the present invention, and an upstream-side exhaust gas introduction unit. The diesel particulate filter is capable of collecting particle matter in exhaust gas exhausted from an internal combustion engine and passing through an exhaust pipe. The particulate matter sensor includes a particle matter accumulation amount calculation unit configured to calculate an amount of particulate matter accumulated in the diesel particulate filter based on the amount of particle matter detected by the particulate matter sensor. The upstream-side exhaust gas introduction unit is configured to introduce a part of the exhaust gas from the exhaust pipe on an upstream side of the diesel particulate filter into the particulate matter sensor.

According to a third aspect of the present invention, an exhaust gas purification apparatus includes a diesel particulate filter, the particulate matter sensor according to the first aspect of the present invention, and a downstream-side exhaust gas introduction unit. The diesel particulate filter is capable of collecting particulate matter in exhaust gas exhausted from an internal combustion engine and passing through an exhaust pipe. The particulate matter sensor includes a filter fault diagnosis unit configured to diagnose whether the diesel particulate filter is in a faulty state based on the amount of particulate matter detected by the particulate matter sensor. The downstream-side exhaust gas introduction unit is configured to introduce a part of the exhaust gas from the exhaust pipe on a downstream side of the diesel particulate filter into the particulate matter sensor.

BRIEF DESCRIPTION OF THE DRAWINGS

Other objects, features, and advantages of the present invention will become more apparent from the following description when read in conjunction with the accompanying drawings, in which.

DESCRIPTION OF THE EMBODIMENTS

Figure 1:
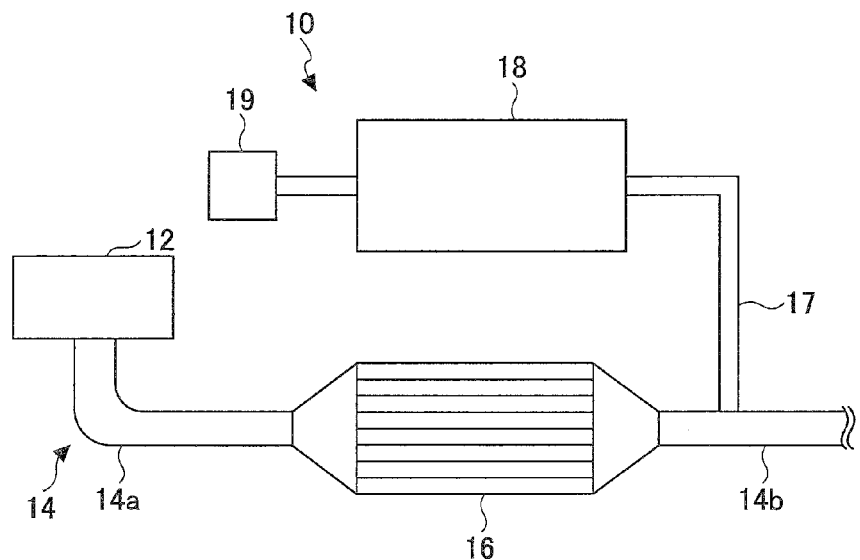
FIG. 1 is a schematic drawing showing a configuration of a whole construction of an exhaust gas purification apparatus according to a first embodiment of the present invention.

According to an embodiment of the present invention, there is provided a particulate matter sensor capable of detecting particle matter in exhaust gas passing through an exhaust gas flow passage. The particulate matter sensor includes a first detection filter provided in the exhaust gas flow passage and capable of collecting the particle matter, a second detection filter provided on a downstream side of the first detection filter in the exhaust gas flow passage and capable of collecting the particle matter, a first differential pressure detection unit detecting a first differential pressure between pressures of an upstream side and the downstream side of the first detection filter, a second differential pressure detection unit detecting a second differential pressure between pressures of an upstream side and a downstream side of the second detection filter, and a particle matter amount detection unit detecting an amount of particle matter based on a detection result of the first differential pressure detection unit and a detection result of the second differential pressure detection unit.

In a conventional particulate matter (PM) measuring method, to regenerate the Diesel Particulate Filter (DPF) by measuring the amount of Particulate Matter (PM) accumulated in the Diesel Particulate Filter (DPF), it is required to calculate the amount of Particulate Matter (PM) accumulated in the detection filter provided in the secondary exhaust pipe by introducing the sample gas into the secondary exhaust pipe. In this case, when the temperature of the sample gas passing through the detection filter in the secondary exhaust pipe changes, the kinetic viscosity of the sample gas changes accordingly and as a result, a friction force is generated between the detection filter and the sample gas; and as a result, the flow velocity of the sample gas is more likely to be changed. The flow rate of sample gas is approximated by the product of the velocity of the sample gas and the cross-sectional area of the exhaust pipe; therefore, when the flow velocity of the sample gas changes, the flow rate of the sample gas is sure to be changed.

Because of this feature, in order to accurately measure the amount of Particulate Matter (PM) accumulated in the detection filter, it is thought to be required to detect a differential pressure between the inlet and the outlet of the detection filter and the temperature of the sample gas and the flow rate of the sample gas passing through the detection filter. To that end, one method may be to provide a pressure sensor, a temperature sensor, and a flow rate sensor as the measuring apparatuses. However, if those three measuring apparatuses are provided (installed), the scale (size) of the measuring apparatuses may become large, which may make it difficult to reduce size and cost of the exhaust gas purification apparatus.

The embodiments of the present invention are made in light of the above circumstances and may become possible to accurately calculate the amount of Particulate Matter (PM) included in exhaust gas without directly detecting the temperature of the exhaust gas and the flow rate of the exhaust gas.

In a particle matter sensor according to an embodiment of the present invention, the two detection filters are provided in series in the exhaust gas flow passage. Further, a ratio between the initial pressure loss (differential pressure) of the first detection filter and the initial pressure loss (differential pressure) of the second detection filter is substantially constant regardless of temperature change of the exhaust gas. Further, it is thought that no particle matter (PM) is accumulated in the second detection filter. Therefore, based on the constant ratio between the initial pressure losses (differential pressure) of the first and the second detection filters and the second differential pressure between the upstream side and the downstream side of the second detection filter provided on the downstream side of the first detection filter, the second differential pressure being detected by the second differential pressure detection unit, it may become possible to estimate the initial pressure loss (differential pressure) of the first detection filter in the current surrounding condition (in the current temperature) without detecting temperature of the exhaust gas. Further, particle matter in exhaust gas is accumulated in the first detection filter and on the upstream side of the second detection filter. In this case, it is thought that the more particle matter accumulated in the first detection filter, the larger the first differential pressure between the pressures of the upstream side and the downstream side of the first detection filter becomes. Further, there is a proportional relationship between the flow rate of exhaust gas passing through the first detection filter and the pressure loss (differential pressure) between the pressures of the upstream side and the downstream side of the first detection filter, where the gradient of the straight lines representing the proportional relationship between the flow rate and the differential pressure changes depending on the amount of Particulate Matter (PM) accumulated in the first detection filter. Namely, it is thought that, when assuming that the amount of particulate matter accumulated in the first detection filter is the same, a ratio between the first differential pressure between the upstream side and the down stream side of the first detection filter provided on the second detection filter before particle matter is accumulated and that after particle matter is accumulated becomes substantially constant regardless of the flow rate of exhaust gas. Because of this feature, by calculating a ratio between the first pressure loss between the pressures of the upstream side and the downstream side of the first detection filter detected by the first differential pressure detection unit and the initial pressure loss (differential pressure) of the first detection filter estimated as described above, based on the value of the ratio, it may become possible to calculate the amount of particulate matter accumulated in the first detection filter provided on the upstream side of the second detection filter without detecting the flow rate of exhaust gas. Therefore, according to an embodiment of the present invention, it may become possible to accurately calculate the amount of particulate matter included in exhaust gas without directly detecting the temperature of the exhaust gas and flow rate of the exhaust gas.

Further, when assuming that the first detection filter and the second detection filter have substantially the same performance, the second differential pressure between the pressures of the upstream side and the down stream side of the second detection filter detected by the second differential pressure detection unit is equal to the first differential pressure between the pressures of the upstream side and the down stream side of the first detection filter detected by the first differential pressure detection unit when there is no particulate matter accumulated in the first detection filter. Therefore, by calculating a difference between the first differential pressure and the second differential pressure, based on the value of the difference, it may become possible to calculate the amount of Particulate Matter (PM) accumulated in the first detection filter without detecting the temperature of the exhaust gas and the flow rate of the exhaust gas. Therefore, according to an embodiment of the present invention, it may become possible to accurately calculate the amount of particulate matter included in exhaust gas without directly detecting the temperature of the exhaust gas and flow rate of the exhaust gas.

Further, according to above the particulate matter sensor according to an embodiment of the present invention, the first detection filter (20,106) and the second detection filter (22, 108) may be provided at substantially the same temperature range in the exhaust gas flow passage (17,102).

Further, the particulate matter sensor according to an embodiment of the present invention may further include a heat retaining unit (200) keeping the temperatures of the first detection filter (20,106) and the second detection filter (22, 108) at substantially the same temperature.

Further, the particulate matter sensor according to an embodiment of the present invention may further include a particle matter removal unit (300) removing particle matter accumulated in the first detection filter (20,106) or the second detection filter (22,108).

In this case, the particle matter removal unit (300) may be a heater or a burner for burning and removing the accumulated particle matter.

Further, in the particulate matter sensor according to an embodiment of the present invention, the particle matter amount detection unit (36,122) may include a first differential pressure initial value estimation unit, based on an initial ratio between the first differential pressure and the second differential pressure and the second differential pressure detected by the second differential pressure detection unit (34,120), estimating an initial value of the first differential pressure in the same conditions where the second differential pressure is detected by the second differential pressure detection unit (34,120), and a ratio calculation unit calculating a ratio between the initial value of the first differential pressure estimated by the first differential pressure initial value estimation unit and the first differential pressure detected by the first differential pressure detection unit (28,114), so that the particle matter amount detection unit (36,122) detects the amount of particle matter based on the ratio calculated by the ratio calculation unit.

Further, in the particulate matter sensor according to an embodiment of the present invention, the first detection filter (20,106) and the second detection filter (22,108) may have substantially the same performance with each other and the particle matter amount detection unit (36,122) may include a difference calculation unit calculating a difference between the first differential pressure detected by the first differential pressure detection unit (28,114) and the second differential pressure detected by the second differential pressure detection unit (34,120) so that the particle matter amount detection unit (36,122) detects the amount of particle matter based on the difference calculated by the difference calculation unit.

Further, in this case, the first detection filter (20,106) and the second detection filter (22,108) may be made as a single formed body.

According to another aspect of the present invention, there is provided an exhaust gas purification apparatus provided in an exhaust pipe (14) through which exhaust gas passes and having a diesel particulate filter (DPF) (16) capable of collecting particle matter in exhaust gas passing through the exhaust pipe (14), the exhaust gas being exhausted from an internal combustion engine (12). The exhaust gas purification apparatus may include the particulate matter sensor (104), and an upstream-side exhaust gas introduction unit (102) introducing a part of the exhaust gas from the exhaust pipe (14) on an upstream side of the diesel particulate filter (DPF) (16) into the particulate matter sensor (104), wherein the particulate matter sensor (104) may include a particle matter accumulation amount calculation unit (122) calculating an amount of particle matter accumulated in the diesel particulate filter (DPF) (16) based on the amount of particle matter detected by the particulate matter sensor (104).

According to still another aspect of the present invention, there is provided an exhaust gas purification apparatus provided in an exhaust pipe (14) through which exhaust gas passes and having a diesel particulate filter (DPF) (16) capable of collecting particle matter in exhaust gas passing through the exhaust pipe (14), the exhaust gas being exhausted from an internal combustion engine (12). The exhaust gas purification apparatus may include the particulate matter sensor (18) and a downstream-side exhaust gas introduction unit (17) introducing a part of the exhaust gas from the exhaust pipe (14) on a downstream side of the diesel particulate filter (DPF) (16) into the particulate matter sensor (18), wherein the particulate matter sensor (18) may include a filter fault diagnosis unit (36) diagnosing whether the diesel particulate filter (DPF) (16) is in a faulty state based on the amount of particle matter detected by the particulate matter sensor(18).

In the following, specific embodiments of the particulate matter sensor and the exhaust gas purification apparatus of the present invention are described with reference to the accompanying drawings.

First Embodiment

Figure 2:
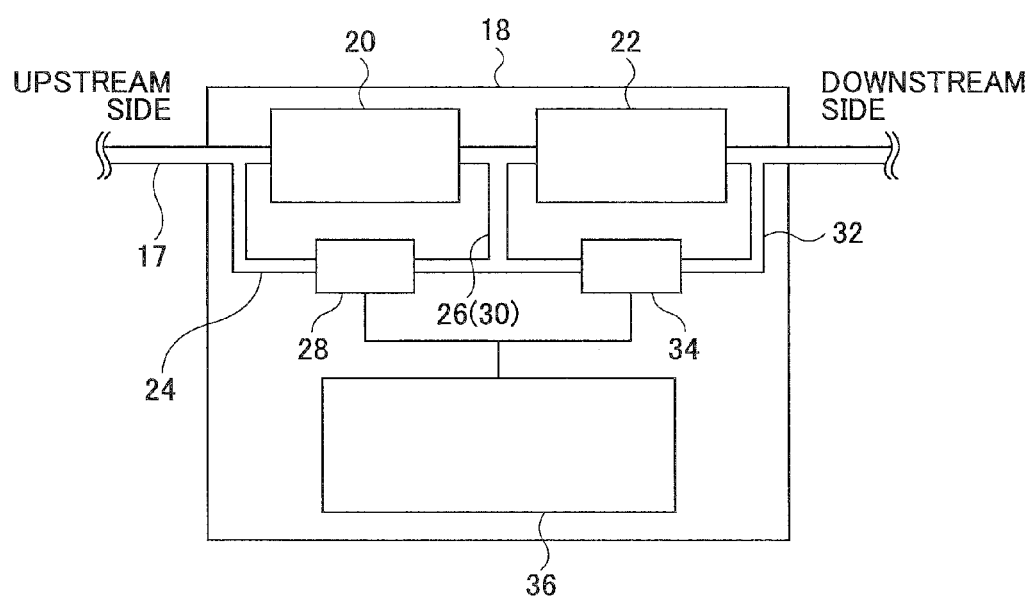
FIG. 2 is a schematic drawing showing a configuration of a main point construction of the exhaust gas purification apparatus according to the first embodiment of the present invention.

FIG. 1 shows an exemplary schematic configuration of a whole construction of an exhaust gas purification apparatus 10 according to a first embodiment of the present invention. FIG. 2 shows an exemplary schematic configuration of a main point construction (fault detection apparatus 18 for detecting fault) of the exhaust gas purification apparatus 10 according to the first embodiment of the present invention.

As FIG. 1 shows, the exhaust gas purification apparatus 10 purifies exhaust gas exhausted from an internal combustion engine (typically a diesel engine) 12. Further, the exhaust gas purification apparatus 10 includes a main exhaust pipe 14 connected to the internal combustion engine 12 and a Diesel Particulate Filter (DPF) 16 provided in the main exhaust pipe 14 and capable of collecting Particulate Matter (PM) included in exhaust gas exhausted from the internal combustion engine 12. Herein, the main exhaust pipe 14 on the upstream side of the Diesel Particulate Filter (DPF) 16 is called a main exhaust pipe 14a and the main exhaust pipe 14 on the downstream side of the Diesel Particulate Filter (DPF) 16 is called a main exhaust pipe 14b.

In this embodiment of the present invention, when a fault of the Diesel Particulate Filter (DPF) 16 is detected, and as a result, an amount of Particulate Matter (PM) leaked to the downstream side of the Diesel Particulate Filter (DPF) 16 becomes greater than a predetermined threshold value, the exhaust gas purification apparatus 10 is able to detect the fault of the Diesel Particulate Filter (DPF) 16 and then give an alarm, turn ON and OFF a lamp, light a lamp or blink a lamp and the like. To that end, the exhaust gas purification apparatus 10 includes a fault detection unit 18 (fault diagnosis unit) capable of detecting a fault of the Diesel Particulate Filter (DPF) 16 (see FIG. 1 and FIG. 2).

Namely, to detect the fault of the Diesel Particulate Filter (DPF) 16, in addition to the main exhaust pipe 14b connected to atmosphere, there is provided an exhaust gas collection line 17 connecting between the fault detection unit (particulate matter sensor) 18 and the downstream side of the Diesel Particulate Filter (DPF) 16 so that exhaust gas on the downstream side of the Diesel Particulate Filter (DPF) 16 is introduced into the fault detection unit 18. In the following, a particulate matter (PM) detection filter (i.e., a testing filter) may be simplified as a detection filter. Further, the exhaust gas collection line 17 is branched from the main exhaust pipe 14b. The size of the cross-sectional area of the exhaust gas collection line 17 is much less than that of the main exhaust pipe 14b (for example, the size of the cross-sectional area of the exhaust gas collection line 17 is about $1/1000$ of that of the main exhaust pipe 14b). The fault detection apparatus 18 detects the fault of the Diesel Particulate Filter (DPF) 16 based on an amount of Particulate Matter (PM) in exhaust gas passing through the exhaust gas collection line 17.

As a Particulate Matter (PM) detection filter, there are provided two particulate matter detection filters (testing filters) 20 and 22 arranged in series in the exhaust gas collection line 17 in the fault detection unit 18. In the following, the particulate matter detection filters (testing filters) 20 and 22 may be simplified as detection filters 20 and 22, respectively. The downstream end of the exhaust gas collection line 17 is connected to a section 19 such as negative-pressure tank, an air intake section where pressure is lower than that at the upstream side of the exhaust gas collection line 17 (i.e., the main exhaust pipe 14b side). Due to the (low-pressure) section 19, a part of exhaust gas passing through the Diesel Particulate Filter (DPF) 16 and in the main exhaust pipe 14b is introduced into the exhaust gas collection line 17 and passes through the detection filters 20 and 22 in this order. In the following, the detection filters 20 and 22 on the upstream side and the downstream side may be referred to as an upstream-side detection filter 20 and a downstream-side detection filter 22, respectively.

In this embodiment of the present invention, the detection filters 20 and 22 are disposed in the exhaust gas collection line 17 where the temperature difference between the temperature of exhaust gas passing through the detection filter 20 and the temperature of exhaust gas passing through the detection filter 22 is minimized as much as possible (preferably where at the same temperature range (distribution) in the exhaust gas collection line 17). By doing this, it is thought that the difference between the temperatures of exhaust gas passing through both the detection filters 20 and 22 is hardly generated. The detection filters 20 and 22 are provided so as to calculate the amount of Particulate Matter (PM) included in exhaust gas and, essentially similar to a laminar flow element, have a configuration so that there is a substantially proportional relationship between the flow rate of the exhaust gas passing through the detection filter and the differential pressure between the pressures of upstream side and the downstream side of the detection filter. Further, the detection filters 20 and 22 are made of a porous ceramic material similar to the Diesel Particulate Filter (DPF) 16 and are capable of collecting Particulate Matter (PM). The detection filter may also be called a porous structure element. Further, the size of the detection filters 20 and 22 is smaller than that of the Diesel Particulate Filter (DPF) 16.

As shown in FIG. 2, in the fault detection apparatus 18, there are provided pressure introducing pipes 24 and 26 so that one end of the pressure introducing pipe 24 is connected to the upstream side of the detection filter 20 and one end of the pressure introducing pipe 26 is connected to the downstream side of the detection filter 20. The other ends of the pressure introducing pipes 24 and 26 are connected to a pressure sensor 28. The pressure sensor 28 detects the pressure applied to the upstream side of the upstream-side detection filter 20 in the exhaust gas collection line 17 through the pressure introducing pipe 24 and the pressure applied to the downstream side of the upstream-side detection filter 20 in the exhaust gas collection line 17 through the pressure introducing pipe 26. Further, the pressure sensor 28 outputs an electrical signal in accordance with the differential pressure between the pressures of the upstream side and the downstream side of the upstream-side detection filter 20 in the exhaust gas collection line 17 (i.e., the differential pressure between the pressures of the inlet and the outlet of the upstream-side detection filter 20).

Further, in the fault detection unit 18, there are provided pressure introducing pipes 30 and 32 so that one end of the pressure introducing pipe 30 is connected to the upstream side of the detection filter 22 and one end of the pressure introducing pipe 32 is connected to the downstream side of the detection filter 22. As shown in FIG. 2, the pressure introducing pipes 30 on the upstream side of the detection filter 22 and the pressure introducing pipes 26 on the downstream side of the detection filter 20 are configured of or partially overlap the same pressure introducing pipe.

The other ends of the pressure introducing pipes 30 and 32 are connected to a pressure sensor 34. The pressure sensor 34 detects the pressure applied to the upstream side of the downstream-side detection filter 22 in the exhaust gas collection line 17 through the pressure introducing pipe 30 and the pressure applied to the downstream side of the downstream-side detection filter 22 in the exhaust gas collection line 17 through the pressure introducing pipe 32. Further, the pressure sensor 34 outputs an electrical signal in accordance with the differential pressure between the pressures of the upstream side and the downstream side of the downstream-side detection filter 22 in the exhaust gas collection line 17 (i.e., the differential pressure between the pressures of the inlet and the outlet of the downstream-side detection filter 22).

In the fault detection unit 18, the pressure sensors 28 and 34 are electrically connected to a calculation section (arithmetic and control unit) 36 having a micro computer as the main component thereof. The outputs of the pressure sensors 28 and 34 are input to the calculation section 36. Based on the output signal from the pressure sensor 28, the calculation section 36 detects the differential pressure "$\Delta Pa$" generated between the pressures of the upstream side and the downstream side of the upstream-side detection filter 20 in the exhaust gas collection line 17. Further, based on the output signal from the pressure sensor 34, the calculation section 36 detects the differential pressure "$\Delta Pb$" generated between the pressures of the upstream side and the downstream side of the downstream-side detection filter 22 in the exhaust gas collection line 17. As the pressure sensors 28 and 34, a diaphram gauge or a known manometer (pressure gauge) such as a strain-gauge-type, Bellows-type, or thermal-type manometer may be used.

Figure 3:
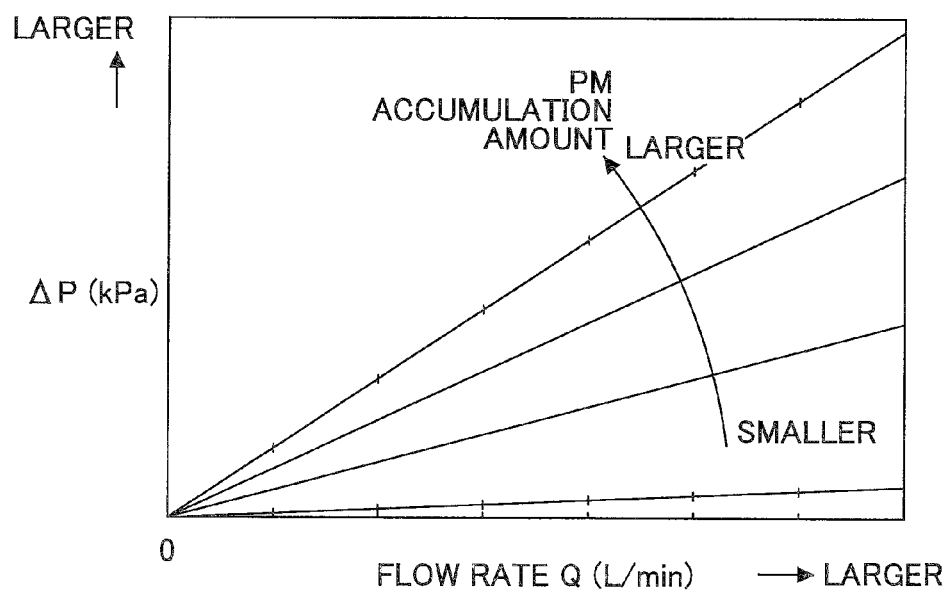
FIG. 3 is a graph showing relationships between flow rate "Q" of exhaust gas passing through a detection filter and differential pressure "$\Delta P$" between the pressures of an upstream side and a downstream side of a detection filter versus a changing amount of Particulate Matter (PM) accumulated on the detection filter.
Figure 4:
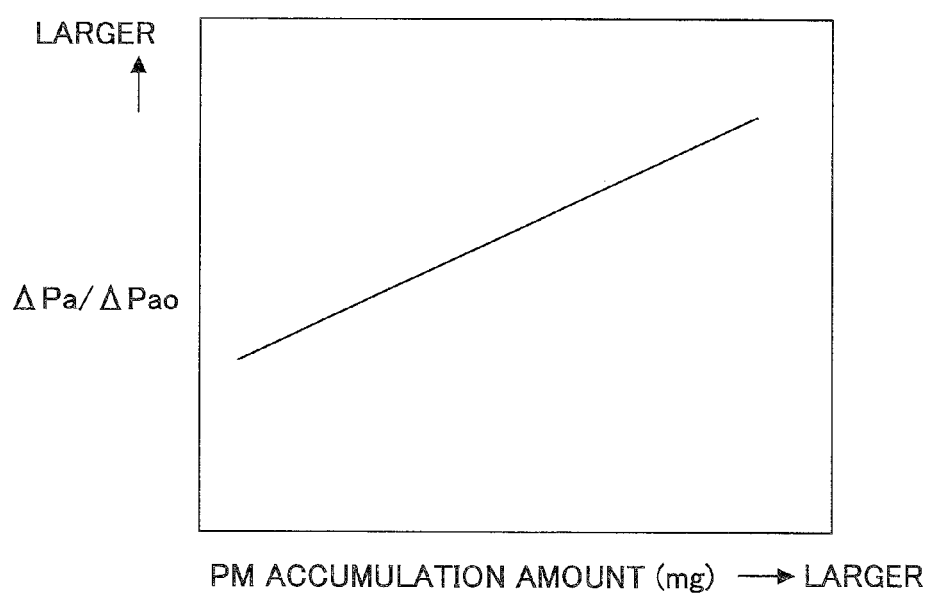
FIG. 4 is a graph showing relationships between a ratio "66 Pa/$\Delta Pa0$" between the differential pressure between the pressures of the upstream side and the downstream side of the detection filter before Particulate Matter (PM) is accumulated "$\Delta Pa0$" and that after Particulate Matter (PM) is accumulated "$\Delta Pa$" and the amount of the Particulate Matter (PM) accumulated in the detection filter.

Next, with reference to FIGS. 3 and 4, operations of the fault detection unit 18 of the exhaust gas purification apparatus 10 according to this embodiment of the present invention are described. FIG. 3 shows relationships between flow rate "Q" of exhaust gas passing through the detection filters 20 and 22 and the differential pressure "$\Delta P$" between the pressures of the upstream-side and the downstream-side of the detection filters 20 and 22 versus a changing amount of Particulate Matter (PM) accumulated on the detection filter 20. FIG. 4 shows relationships between a ratio "$\Delta Pa/\Delta Pa0$" of the differential pressure "$\Delta Pa$" between the pressures of the upstream side and the downstream side of the detection filter 20 after Particulate Matter (PM) is accumulated to that 37 $\Delta Pa0$" before Particulate Matter (PM) is accumulated and the amount of the Particulate Matter (PM) accumulated on the detection filter 20.

In this embodiment, after passing through the main exhaust pipe 14a, the Diesel Particulate Filter (DPF) 16 and the main exhaust pipe 14b in this order, exhaust gas exhausted from the internal combustion engine 12 is discharged to atmosphere or introduced into the detection filters 20 and 22 through the exhaust gas collection line 17. Namely, most of exhaust gas having passed through the Diesel Particulate Filter (DPF) 16 is discharged to atmosphere through the main exhaust pipe 14b and a part of exhaust gas having passed through the Diesel Particulate Filter (DPF) 16 is introduced into the detection filters 20 and 22 through the exhaust gas collection line 17.

As described above, the detection filters 20 and 22 have the configuration so that there is a substantially proportional relationship between the flow rate of the exhaust gas passing through the detection filters and the differential pressure between the pressures of upstream side and the downstream side of the detection filters. Because of this feature, the flow rate "Q" of laminar flow of exhaust gas passing through the exhaust gas collection line 17 can be expressed by the following formula 1. In the formula 1, the symbol "r" denotes the inner diameter of the exhaust gas collection line 17, the symbol "$\Delta P$" denotes the differential pressure between the pressures of the upstream side and the downstream side of the detection filters 20 and 22, the symbol "$\eta$" denotes the kinetic viscosity of exhaust gas, and the symbol "L" denotes the length of the exhaust gas collection line 17 in the flow direction.

$$Q = \pi \cdot r^4 \cdot \Delta P / (8 \cdot \eta \cdot L) \tag{1}$$

Since the flow path shape of the exhaust gas collection line 17 is hardly changed, the above symbols "r" and "L" can be regarded as fixed values. As a result, the formula 1 can be modified into the following formula 2.

$$\Delta P = Q \cdot \eta / K \tag{2}$$

wherein $K = \pi \cdot r^4/(8 \cdot L)$

When the temperature of exhaust gas changes, the kinetic viscosity "$\eta$" of the exhaust gas changes accordingly. In this case, there is a substantially proportional relationship between the temperature of the exhaust gas and the kinetic viscosity "$\eta$" of the exhaust gas. Further, when the kinetic viscosity "$\eta$" of the exhaust gas changes, the flow rate "Q" of the exhaust gas changes or the differential pressure "$\Delta P$" between the pressures of the upstream side and the downstream side of the detection filters 20 and 22 changes. Namely, the gradient of the straight lines representing the proportional relationship between the flow rate "Q" and the differential pressure "$\Delta P$" changes depending on the temperature of exhaust gas.

Further, when the temperature of exhaust gas changes, an initial pressure loss "$\Delta Pa0$" (i.e., an initial value of the differential pressure between the pressures of the upstream side and the downstream side of the detection filter 20 before Particulate Matter (PM) is accumulated) of the detection filter 20 and an initial pressure loss "$\Delta Pb0$" of the detection filter 22 change. However, when assuming that the initial pressure losses "$\Delta Pa0$" and "$\Delta Pb0$" change at the same rate as each other, a ratio of the initial pressure losses "$\alpha$"0 (=$\Delta Pa0/\Delta Pb0$) (herein may be referred to as "initial ratio") remains the same value. This is also the result when using the following formula (3) derived from formula (2).

$$\alpha = \Delta Pa0/\Delta Pb0 \tag{3}$$
$$= (Qa/Qb) \cdot (\eta a/\eta b) \cdot (Ka/Kb)$$

In formula (3), first, the term (Ka/Kb) is a constant value regardless of temperature change of the exhaust gas; secondly, the term ($\eta a/\eta b$) is substantially unchanged regardless of the temperature change because the temperatures of exhaust gas passing through both the detection filters 20 and 22 are substantially the same though there is a substantially proportional relationship between the temperature of the exhaust gas and the kinetic viscosity "$\eta$" of the exhaust gas (A value of kinetic viscosity "$\eta a$" of exhaust gas passing through the detection filter 20 is substantially equal to a value of kinetic viscosity "$\eta b$" of exhaust gas passing through the detection filter 22); and thirdly, the term (Qa/Qb) is also substantially unchanged regardless of the temperature change because the temperatures of exhaust gas passing through both the detection filters 20 and 22 are substantially the same though there is a substantially proportional relationship between the temperature and the flow rate "Q" of the exhaust gas (A value of flow rate "Qa" of exhaust gas passing through the detection filter 20 is substantially equal to a value of flow rate "Qb" of exhaust gas passing through the detection filter 22). Therefore, it is thought that, even when the temperature of exhaust gas changes, the initial ratio "α"(=ΔPa0/ΔPb0) is unchanged.

By using this feature (based on formula (3)), the initial pressure loss "ΔPa0"0 of the upstream-side detection filter 20 may be calculated based on the initial pressure loss "ΔPb0" downstream-side detection filter 22 and the initial ratio "α" which is a constant value regardless of temperature change (e.g., ΔPa0=ΔPb019 α). Further, it is assumed that Particulate Matter (PM) is not accumulated in the downstream-side detection filter 22, the pressure loss (differential pressure) "ΔPb" between the pressures of the upstream side and the downstream side of the downstream-side detection filter 22 is thought to be almost the same as the initial pressure loss "ΔPb0" of the downstream-side detection filter 22 in the same surroundings. Therefore, based on the pressure loss (differential pressure) "ΔPb" between the pressures of the upstream side and the downstream side of the downstream-side detection filter 22 in certain conditions, it may become possible to obtain the initial pressure loss "ΔPb0" of the downstream-side detection filter 22 in the same surroundings. As a result, based on the initial ratio "α" which is a constant value regardless of temperature change and the pressure loss (differential pressure) "ΔPb" between the pressures of the upstream side and the downstream side of the downstream-side detection filter 22 in certain conditions, it may become possible to estimate the initial pressure loss "ΔPa0" of the upstream-side detection filter 20 at the same condition when the pressure loss (differential pressure) "ΔPb" of the downstream-side detection filter 22 is detected using the pressure sensor 34 without detecting the temperature of the exhaust gas.

Further, the upstream-side detection filter 20 is able to collect Particulate Matter (PM) in exhaust gas having passed through the Diesel Particulate Filter (DPF) 16 and the Particulate Matter (PM) in exhaust does not flow (leak) to the downstream side of the upstream-side detection filter 20; as a result, exhaust gas not including Particulate Matter (PM) passes through the downstream-side detection filter 22. As described above, Particulate Matter (PM) is accumulated in the upstream-side detection filter 20. As the amount of Particulate Matter (PM) accumulated in the upstream-side detection filter 20 increases, the pressure loss (differential pressure) "ΔPa" between the pressures of the upstream side and the downstream side of the upstream-side detection filter 20 increases accordingly. In this case, when a ratio "β" is defined as β=66 Pa/ΔPa0, wherein, as described above, the symbol "ΔPa" denotes the pressure loss (differential pressure) between the pressures of the upstream side and the downstream side of the upstream-side detection filter 20 and the symbol "ΔPa0" denotes the initial value of the pressure loss (differential pressure) (i.e., the initial pressure loss) between the pressures of the upstream side and the downstream side of the upstream-side detection filter 20 before Particulate Matter (PM) is accumulated in the upstream-side detection filter 20. In this case, the value of the ratio "β" changes in proportion to the amount of Particulate Matter (PM) accumulated in the upstream-side detection filter 20 (see FIG. 4).

Further, there is a proportional relationship between the flow rate "Qa" of exhaust gas passing through the upstream-side detection filter 20 and the pressure loss (differential pressure) "ΔPa" between the pressures of the upstream side and the downstream side of the upstream-side detection filter 20, where the gradient of the straight lines representing the relationships between the flow rate "Q" and the differential pressure "ΔPa" changes depending on the amount of Particulate Matter (PM) accumulated in the upstream-side detection filter 20 (see FIG. 3). Namely, the ratio "β" (which is defined as 62 =ΔPa/ΔPa0, wherein, the symbols "ΔPa" and "ΔPa0" denote the pressure loss (differential pressure) between the pressures of the upstream side and the downstream side of the upstream-side detection filter 20 after and before, respectively, Particulate Matter (PM) is accumulated in the upstream-side detection filter 20) is a substantially constant value regardless of the change in flow rate "Qa" of exhaust gas when assuming that the amount of Particulate Matter (PM) accumulated in the upstream-side detection filter 20 is unchanged. By using this feature, when the ratio "β" is calculated, based on the value of the ratio "β", it may become possible to calculate the amount of Particulate Matter (PM) accumulated in the upstream-side detection filter 20 without detecting the flow rate "Qa" of exhaust gas.

To that end, in this embodiment of the present invention, the calculation section 36 periodically detects the pressure loss (differential pressure) "ΔPa" between the pressures of the upstream side and the downstream side of the upstream-side detection filter 20 in the exhaust gas collection line 17 based on the output signal from the pressure sensor 28. Further, the calculation section 36 periodically detects the pressure loss (differential pressure) "ΔPb" between the pressures of the upstream side and the downstream side of the downstream-side detection filter 22 in the exhaust gas collection line 17 based on the output signal from the pressure sensor 34.

Then, based on the ratio "α"(=ΔPa0/ΔPb0) between the initial pressure losses of the detection filters 20 and 22 (more specifically, when the Particulate Matter (PM) is not yet accumulated in the detection filters 20 and 22 (for example, just after the exhaust gas purification apparatus 10 is manufactured), the initial ratio "α" of the pressure loss (differential pressure) "ΔPa" between the pressures of the upstream side and the downstream side of the upstream-side detection filter 20 by using the output signal from the pressure sensors 28 to the pressure loss (differential pressure) "ΔPb" between the pressures of the upstream side and the downstream side of the downstream-side detection filter 22 by using the output signal from the pressure sensors 34) and the pressure loss (differential pressure) "ΔPb" between the pressures of the upstream side and the downstream side of the downstream-side detection filter 22 by using the output signal from the pressure sensors 34, the calculation section 36 estimates the initial pressure loss (differential pressure) "ΔPa0" between the pressures of the upstream side and the downstream side of the upstream-side detection filter 20 at the current condition (namely, under the same temperature condition as that when the pressure loss (differential pressure) "ΔPb" is detected by using the output signal from the pressure sensors 34).

Next, based on the estimated initial pressure loss (differential pressure) "ΔPa0" between the pressures of the upstream side and the downstream side of the upstream-side detection filter 20 and the pressure loss (differential pressure) "ΔPa" between the pressures of the upstream side and the downstream side of the upstream-side detection filter 20 by using the output signal from the pressure sensor 28, the calculation section 36 estimates the ratio "β"(=ΔPa/ΔPa0). Then, based on the value of the ratio "β", by referring to the relationship between the previously determined ratio "β" and the amount of Particulate Matter (PM) accumulated in the upstream-side detection filter 20, the calculation section 36 calculates the amount of Particulate Matter (PM) accumulated in the upstream-side detection filter 20.

As described above, according to this embodiment of the present invention, to calculate the amount of Particulate Matter (PM) accumulated in the upstream-side detection filter 20, it is thought that what may be necessary is to detect the pressure losses (differences) "ΔPa" and "ΔPb" between the pressures of the upstream side and the downstream side of the upstream-side detection filter 20 and the downstream-side detection filter 22, respectively, which are connected in series in the exhaust gas collection line 17 without detecting any of the temperature of exhaust gas and the flow rate of flowing exhaust gas. Therefore, according to this embodiment of the present invention, by using the pressure losses (differences) "ΔPa" and "ΔPb" detected by the pressure sensors 28 and 34, respectively, without detecting any of the temperature of exhaust gas and the flow rate of flowing exhaust gas, namely without mounting (installing) any of a temperature sensor of the exhaust gas and a flow rate sensor of the exhaust gas, it may become possible to accurately calculate the amount of Particulate Matter (PM) accumulated in the upstream-side detection filter 20. As a result, according to this embodiment of the present invention, it may become possible to reduce the size and cost of the exhaust gas purification apparatus 10 and the fault detection unit 18.

In the fault detection unit 18 according to this embodiment of the present invention, as described above, the calculation section 36 calculates the amount of Particulate Matter (PM) accumulated in the upstream-side detection filter 20. Then, based on the amount of Particulate Matter (PM) accumulated in the upstream-side detection filter 20, the calculation section 36 further calculates the amount of Particulate Matter (PM) included in exhaust gas flowing in the main exhaust pipe 14b on the downstream side of the Diesel Particulate Filter (DPF) 16 and determines whether the amount of Particulate Matter (PM) leaked to the downstream side of the Diesel Particulate Filter (DPF) 16 is equal to or more than a predetermined threshold value to determine whether the Diesel Particulate Filter (DPF) 16 is in a faulty state. When determining that the Diesel Particulate Filter (DPF) 16 is in a faulty state based on the calculated amount of Particulate Matter (PM) accumulated in the upstream-side detection filter 20, the exhaust gas purification apparatus 10 gives an alarm, turns ON and OFF, light a lamp and the like. Therefore, according to this embodiment of the present invention, it may become possible to determine whether the Particulate Filter (DPF) 16 is in a faulty state by calculating an amount of Particulate Matter (PM) accumulated in the upstream-side detection filter 20 and further calculating the amount of Particulate Matter (PM) included in exhaust gas flowing on the downstream side of the Diesel Particulate Filter (DPF) 16, and when determining that the Diesel Particulate Filter (DPF) 16 is in a faulty state, the fault of the Diesel Particulate Filter (DPF) 16 may be notified to the driver of the vehicle or the like including the exhaust gas purification apparatus 10 according to this embodiment of the present invention.

Further, according to this embodiment of the present invention, as described above, the pressure introducing pipes 30 on the upstream side of the detection filter 22 and the pressure introducing pipes 26 on the downstream side of the detection filter 20 are configured of or partially overlap the same pressure introducing pipe. Because of this feature, it may become possible to reduce the size and the cost of the fault detection unit 18.

Second Embodiment

Figure 5:
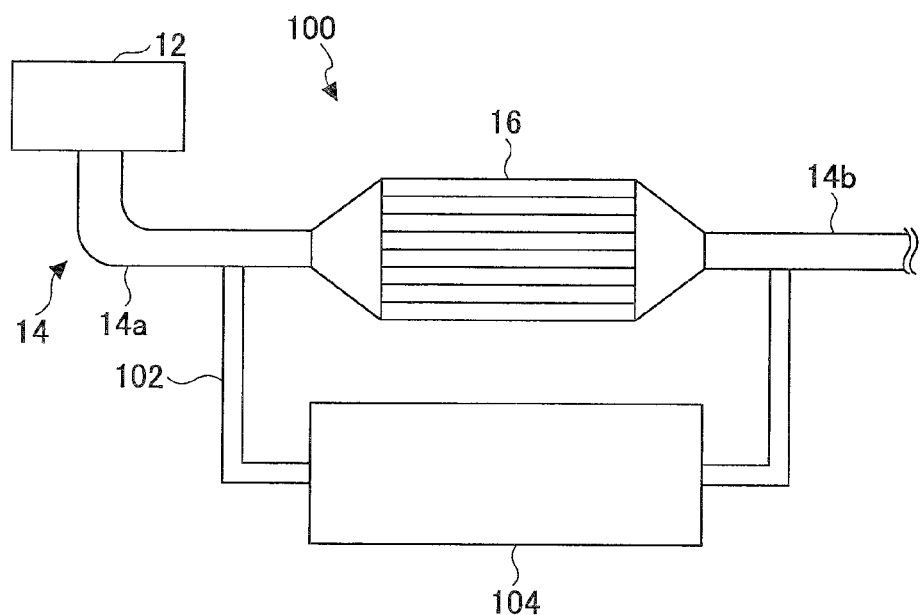
FIG. 5 is a schematic drawing showing a configuration of a whole construction of the exhaust gas purification apparatus according to a second embodiment of the present invention.
Figure 6:
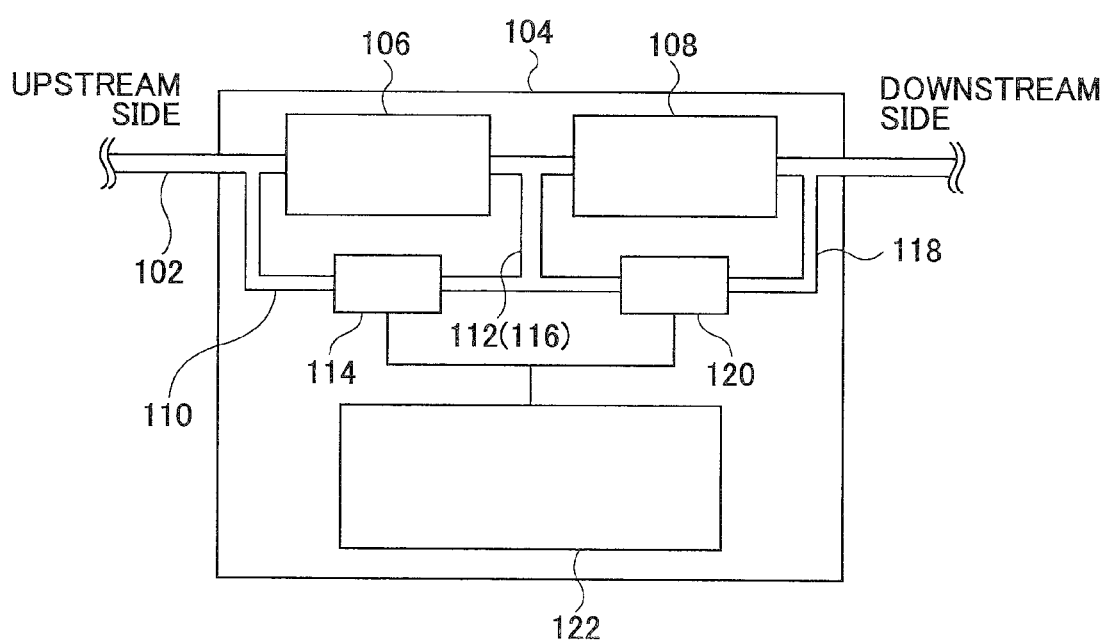
FIG. 6 is a schematic drawing showing a configuration of a main point construction of the exhaust gas purification apparatus according to the second embodiment of the present invention.

FIG. 5 shows an exemplary schematic configuration of a whole construction an exhaust gas purification apparatus 100 according to a second embodiment of the present invention. FIG. 6 shows an exemplary schematic configuration of a main point construction of the exhaust gas purification apparatus 100. Throughout the figures, the same reference numerals are repeatedly used for the same or equivalent elements and the descriptions thereof may be omitted or simplified.

As FIG. 5 shows, the exhaust gas purification apparatus 100 includes the Diesel Particulate Filter (DPF) 16 to convert exhaust gas exhausted from the internal combustion engine (typically a diesel engine) 12. Further, the exhaust gas purification apparatus 100 includes the measurement unit (particulate matter sensor) 104 capable of measuring the amount of Particulate Matter (PM) accumulated in the Diesel Particulate Filter (DPF) 16. Further, when determining that the measured amount of Particulate Matter (PM) is equal to or greater than a threshold value, exhaust gas purification apparatus 100 may burn and oxidize the Particulate Matter (PM) accumulated in the Diesel Particulate Filter (DPF) 16 to regenerate the Diesel Particulate Filter (DPF) 16.

To measure the amount of Particulate Matter (PM) accumulated in the Diesel Particulate Filter (DPF) 16, as shown in FIG. 5, in addition to the main exhaust pipe 14, there is provided an exhaust gas collection line 102 connecting between the measurement unit 104 and the upstream side of the Diesel Particulate Filter (DPF) 16 as upstream-side exhaust gas introduction means to introduce exhaust gas on the upstream side of the Diesel Particulate Filter (DPF) 16 into the measurement unit 104. Namely, the exhaust gas collection line 102 is branched from the main exhaust pipe 14a. The size of the cross-sectional area of the exhaust gas collection line 102 is much less than that of the main exhaust pipe 14a (for example, the size of the cross-sectional area of the exhaust gas collection line 102 is about $\frac{1}{1000}$ of that of the main exhaust pipe 14a). The measurement apparatus 104 measures the amount of Particulate Matter (PM) accumulated in the Diesel Particulate Filter (DPF) 16 based on an amount of Particulate Matter (PM) in exhaust gas passing through the exhaust gas collection line 102.

As shown in FIG. 6, as a Particulate Matter (PM) detection filter, there are provided two detection (testing) filters 106 and 108 arranged in series in the exhaust gas collection line 102 in the measurement unit 104. The downstream end of the exhaust gas collection line 102 is connected to the downstream side of the Diesel Particulate Filter (DPF) 16 in the main exhaust pipe 14 (i.e., main exhaust pipe 14b). As a result, the exhaust gas collection line 102 is connected in parallel with the main exhaust pipe 14. Due to this parallel connection, a part of exhaust gas exhausted from the internal combustion engine 12 is introduced from the main exhaust pipe 14a into the exhaust gas collection line 102 and passes through the detection filters 106 and 108 in this order and is mixed with the exhaust gas having passed through the Diesel Particulate Filter (DPF) 16 on the downstream side of the Diesel Particulate Filter (DPF) 16 in the main exhaust pipe 14b. In the following, the detection filters 106 and 108 on the upstream side and the downstream side in the exhaust gas collection line 102 may be referred to as an upstream-side detection filter 106 and a downstream-side detection filter 108, respectively.

In this embodiment, the detection filters 106 and 108 are disposed in the exhaust gas collection line 102 where the temperature difference between the temperatures of exhaust gas passing through the detection filter 106 and the detection filter 108 is minimized as much as possible (preferably at the same temperature range (distribution) in the exhaust gas collection line 102). By doing this, it is thought that the difference between the temperatures of exhaust gas passing through both the detection filters 106 and 108 is hardly generated. The detection filters 106 and 108 are provided so as to calculate the amount of Particulate Matter (PM) included in exhaust gas and, essentially similar to a laminar flow element, have a configuration so that there is a substantially proportional relationship between the flow rate of the exhaust gas passing through the detection filter and the differential pressure between the pressures of upstream side and the downstream side of the detection filter. Further, the detection filters 106 and 108 are made of a porous ceramic material or the like similar to the Diesel Particulate Filter (DPF) 16 and are capable of collecting Particulate Matter (PM). Further, the size of the detection filters 106 and 108 is smaller than that of the Diesel Particulate Filter (DPF) 16.

As shown in FIG. 6, in the measurement unit 104, there are provided pressure introducing pipes 110 and 112 so that one end of the pressure introducing pipe 110 is connected to the upstream side of the detection filter 106 and one end of the pressure introducing pipe 112 is connected to the downstream side of the detection filter 106. The other ends of the pressure introducing pipes 110 and 112 are connected to a pressure sensor 114. The pressure sensor 114 detects the pressure applied to the upstream side of the upstream-side detection filter 106 in the exhaust gas collection line 102 through the pressure introducing pipe 110 and the pressure applied to the downstream side of the upstream-side detection filter 106 in the exhaust gas collection line 102 through the pressure introducing pipe 112. Further, the pressure sensor 114 outputs an electrical signal in accordance with the differential pressure between the pressures of the upstream side and the downstream side of the upstream-side detection filter 106 in the exhaust gas collection line 102 (i.e., the differential pressure between the pressures of the inlet and the outlet of the upstream-side detection filter 106).

Further, in the measurement unit 104, there are provided pressure introducing pipes 116 and 118 so that one end of the pressure introducing pipe 116 is connected to the upstream side of the detection filter 108 and one end of the pressure introducing pipe 118 is connected to the downstream side of the detection filter 108. As shown in FIG. 6, the pressure introducing pipes 116 on the upstream side of the detection filter 108 and the pressure introducing pipes 112 on the downstream side of the detection filter 106 are configured of or partially overlap the same pressure introducing pipe.

The other ends of the pressure introducing pipes 116 and 118 are connected to a pressure sensor 120. The pressure sensor 120 detects the pressure applied to the upstream side of the downstream-side detection filter 108 in the exhaust gas collection line 102 through the pressure introducing pipe 116 and the pressure applied to the downstream side of the downstream-side detection filter 108 in the exhaust gas collection line 102 through the pressure introducing pipe 118. Further, the pressure sensor 120 outputs an electrical signal in accordance with the differential pressure between the pressures of the upstream side and the downstream side of the downstream-side detection filter 108 in the exhaust gas collection line 102 (i.e., the differential pressure between the pressures of the inlet and the outlet of the downstream-side detection filter 108).

In the measurement unit 104, the pressure sensors 114 and 120 are electrically connected to the calculation section (arithmetic and control unit) 122 having a micro computer as the main component thereof. The outputs of the pressure sensors 114 and 120 are input to the calculation section 122. Based on the output signal from the pressure sensor 114, the calculation section 122 detects the differential pressure "$\Delta Pa$" generated between the pressures of the upstream side and the downstream side of the upstream-side detection filter 106 in the exhaust gas collection line 102. Further, based on the output signal from the pressure sensor 120, the calculation section 122 detects the differential pressure $\Delta Pb$ generated between the pressures of the upstream side and the downstream side of the downstream-side detection filter 108 in the exhaust gas collection line 102. As the pressure sensors 114 and 120, a diaphragm gauge or a known manometer (pressure gauge) such as a strain-gauge-type, Bellows-type, or thermal-type manometer may be used.

Next, operations of the measurement unit 104 of the exhaust gas purification apparatus 100 according to this embodiment of the present invention are described.

In this embodiment, most exhaust gas exhausted from the internal combustion engine 12 passes through the main exhaust pipe 14a, the Diesel Particulate Filter (DPF) 16, and the main exhaust pipe 14b in this order and is discharged to atmosphere; a part (rest) of exhaust gas exhausted from the internal combustion engine 12 is introduced from the main exhaust pipe 14a into the exhaust gas collection line 102, passed through the detection filters 106 and 108 in this order and introduced into the main exhaust pipe 14b to be discharged to atmosphere.

Similar to the detection filters 20 and 22, the detection filters 106 and 108 have the configuration so that there is a substantially proportional relationship between the flow rate of the exhaust gas passing through the detection filter and the differential pressure (pressure loss) between the pressures of the upstream side and the downstream side of the detection filter. Because of this feature, the flow rate "Q" of laminar flow of exhaust gas passing through the exhaust gas collection line 102 can be expressed by the above formula 1. Therefore, in this embodiment of the present invention as well, based on the initial pressure loss ratio "α" which is a constant value regardless of temperature change of the detection filters 106 and 108 and the pressure loss (differential pressure) "$\Delta Pb$" between the pressures of the upstream side and the downstream side of the downstream-side detection filter 108 based on the output signal from the pressure sensor 120 in the current conditions (current surroundings), it may become possible to estimate the initial pressure loss "$\Delta Pa0$" of the upstream-side detection filter 106 in the same condition (same surroundings) as that when the pressure loss (differential pressure) "$\Delta Pb$" of the downstream-side detection filter 108 is detected using the pressure sensor 120 without detecting the temperature of the exhaust gas. Further, based on the ratio "β"(32 $\Delta Pa/\Delta Pa0$) of a value of "$\Delta Pa$" which is the pressure loss (differential pressure) in the same condition (same surroundings) between the pressures of the upstream side and the downstream side of the upstream-side detection filter 106 based on the output signal of the pressure sensor 114 to a value of "$\Delta Pa0$" which is the initial value of the pressure loss (differential pressure) (i.e., the initial pressure loss) between the pressures of the upstream side and the downstream side of the upstream-side detection filter 106 before Particulate Matter (PM) is accumulated, it may become possible to calculate the amount of Particulate Matter (PM) accumulated in the upstream-side detection filter 106 without detecting the flow rate "Qa" of exhaust gas.

To that end, in this embodiment of the present invention, the calculation section 122 periodically detects the pressure loss (differential pressure) "$\Delta Pa$" between the pressures of the upstream side and the downstream side of the upstream-side detection filter 106 in the exhaust gas collection line 102 based on the output signal from the pressure sensors 114. Further, the calculation section 122 periodically detects the pressure loss (differential pressure) "$\Delta Pb$" between the pressures of the upstream side and the downstream side of the downstream-side detection filter 108 in the exhaust gas collection line 102 based on the output signal from the pressure sensors 120.

Then, based on the ratio "60 "(=$\Delta Pa0/\Delta Pb0$) between the initial pressure losses of the detection filters 106 and 108

(more specifically, when the Particulate Matter (PM) is not yet accumulated in the detection filters 106 and 108 (for example, just after the exhaust gas purification apparatus 100 is manufactured), the initial ratio "α" of the pressure loss (differential pressure) "ΔPa" between the pressures of the upstream side and the downstream side of the upstream-side detection filter 106 by using the output signal from the pressure sensors 114 to the pressure loss (differential pressure) "ΔPb" between the pressures of the upstream side and the downstream side of the downstream-side detection filter 108 by using the output signal from the pressure sensors 120) and the pressure loss (differential pressure) "ΔPb" between the pressures of the upstream side and the downstream side of the downstream-side detection filter 108 by using the output signal from the pressure sensors 120, the calculation section 122 estimates the initial pressure loss (differential pressure) "ΔPa0" between the pressures of the upstream side and the downstream side of the upstream-side detection filter 106 in the current condition (current surroundings) (i.e., under the same temperature condition (same temperature surroundings) as that when the pressure loss (differential pressure) "ΔPb" is detected by using the output signal from the pressure sensors 120).

Next, based on the estimated initial pressure loss (differential pressure) "ΔPa0" and the pressure loss (differential pressure) "ΔPa" between the pressures of the upstream side and the downstream side of the upstream-side detection filter 106 by using the output signal from the pressure sensors 114, the calculation section 122 estimates the ratio "β"(=ΔPa/ΔPa0). Then, based on the value of the ratio "β", by referring to the relationship between the previously determined ratio "β" and the amount of Particulate Matter (PM) accumulated in the upstream-side detection filter 106, the calculation section 122 calculates the amount of Particulate Matter (PM) accumulated in the upstream-side detection filter 106.

As described above, according to this embodiment of the present invention, it is thought that, to calculate the amount of Particulate Matter (PM) accumulated in the upstream-side detection filter 106, what is necessary is to detect the pressure losses (differences) "ΔPa" and "ΔPb" between the pressures of the upstream side and the downstream side of the upstream-side detection filter 106 and the downstream-side detection filter 108, respectively, which are connected in series in the exhaust gas collection line 102 without detecting any of the temperature of exhaust gas and the flow rate of flowing exhaust gas. Therefore, according to this embodiment of the present invention, by using the pressure losses (differences) "ΔPa" and "ΔPb" detected by the pressure sensors 114 and 120, respectively, without detecting any of the temperature of exhaust gas and the flow rate of flowing exhaust gas, namely without mounting (installing) a temperature sensor of the exhaust gas and a flow rate sensor of the exhaust gas, it may become possible to accurately calculate the amount of Particulate Matter (PM) accumulated in the upstream-side detection filter 106. As a result, according to this embodiment of the present invention, it may become possible to reduce the size and cost of the exhaust gas purification apparatus 100 and the measurement unit 104.

In the measurement unit 104 according to this embodiment of the present invention, as described above, the calculation section 122 calculates the amount of Particulate Matter (PM) accumulated in the upstream-side detection filter 106. Then, based on the amount of Particulate Matter (PM) accumulated in the upstream-side detection filter 106, the calculation section 122 further calculates the amount of Particulate Matter (PM) included in exhaust gas flowing in the main exhaust pipe 14a on the upstream side of the Diesel Particulate Filter (DPF) 16 to calculate (estimate) the amount of Particulate Matter (PM) accumulated in the Diesel Particulate Filter (DPF) 16. Then, when determining that the calculated amount of Particulate Matter (PM) accumulated in the upstream-side detection filter 106 exceeds a predetermined threshold value, the exhaust gas purification apparatus 100 determines that the amount of Particulate Matter (PM) accumulated in the Diesel Particulate Filter (DPF) 16 exceeds a predetermined threshold value and burns and oxidizes the Particulate Matter (PM) accumulated in the Diesel Particulate Filter (DPF) 16 to remove the Particulate Matter (PM) from the Diesel Particulate Filter (DPF) 16. More specifically, for example, the exhaust gas purification apparatus 100 causes the internal combustion engine 12 to exhaust higher-temperature exhaust gas to remove the Particulate Matter (PM) from the Diesel Particulate Filter (DPF) 16. Therefore, according to this embodiment of the present invention, the amount of Particulate Matter (PM) accumulated in the upstream-side detection filter 106 is calculated to estimate the amount of Particulate Matter (PM) accumulated in the Diesel Particulate Filter (DPF) 16, and when determining that the amount of Particulate Matter (PM) accumulated in the Diesel Particulate Filter (DPF) 16 exceeds a predetermined threshold value, the Diesel Particulate Filter (DPF) 16 may be regenerated by removing the Particulate Matter (PM) accumulated in the Diesel Particulate Filter (DPF) 16.

Further, according to this embodiment of the present invention, as described above, the pressure introducing pipes 116 on the upstream side of the detection filter 108 and the pressure introducing pipes 112 on the downstream side of the detection filter 106 are configured of or partially overlap the same pressure introducing pipe. Because of this feature, it may become possible to reduce the size and the cost of the measurement unit 104.

Third Embodiment

In the above first embodiment, it is not assumed that the performance and the shape of the upstream-side detection filter 20 are the same as those of the downstream-side detection filter 22. On the other hand, in a third embodiment of the present invention, it is assumed that the performance and the shape of the upstream-side detection filter 20 are the same as those of the downstream-side detection filter 22. In the following, the same reference numerals are used for the same or equivalent elements described in the first embodiment of the present invention and the descriptions thereof may be omitted.

Namely, in this embodiment of the present invention, it is assumed that the upstream-side detection filter 20 and the downstream-side detection filter 22 are made as a single formed (molded) body or the like so as to have the same performance and shape (including, for example, the same thickness, the same PM collection area, the same kinetic viscosity and the like). Further, it is assumed that the detection filters 20 and 22 are arranged to be close to each other so that there is little difference between the temperatures of exhaust gas in the detection filters 20 and 22.

Because of these features, in this embodiment, it is thought that a value of the initial pressure loss (differential pressure) "ΔPa0" of the upstream-side detection filter 20 and a value of the initial pressure loss (differential pressure) "ΔPb0" of the downstream-side detection filter 22 are substantially the same (i.e., ΔPa0 is nearly equal to ΔPa0); and the difference between the temperatures of the detection filters is always almost zero. Further, as described above, it is assumed that Particulate Matter (PM) is not accumulated in the downstream-side detection filter 22; therefore, it is thought that the pressure loss (differential pressure) "ΔPb" between the pressures of the upstream side and the downstream side of the downstream-side detection filter 22 is almost the same as the initial pressure loss "ΔPb0" of the downstream-side detection filter 22.

Therefore, based on the pressure loss (differential pressure) "ΔPb" between the pressures of the upstream side and the downstream side of the downstream-side detection filter 22 using the pressure sensor 34 in the current conditions (current surroundings), it may become possible to obtain the initial pressure loss "ΔPb0" of the downstream-side detection filter 22 in the same conditions (same surroundings), and further it may become possible to obtain the initial pressure loss "ΔPa0" of the upstream-side detection filter 20 in the same conditions (same surroundings). Namely, based on the pressure loss (differential pressure) "ΔPb" of the downstream-side detection filter 22 using the pressure sensor 34 in the current conditions (current surroundings), it may become possible to estimate the initial pressure loss 37 ΔPa0" of the upstream-side detection filter 20 in the same conditions (same surroundings) where the pressure loss (differential pressure) "ΔPb" of the downstream-side detection filter 22 is detected using the pressure sensor 34 without detecting temperature of the exhaust gas.

Further, as described above, it is thought that Particulate Matter (PM) included in exhaust gas is accumulated in the upstream-side detection filter 20 but is not accumulated in the downstream-side detection filter 22. Further, the more the amount of Particulate Matter (PM) accumulated in the upstream-side detection filter 20 becomes, the more likely the initial pressure loss (differential pressure) "ΔPa0" between the pressures of the upstream side and the downstream side of the upstream-side detection filter 20 becomes. Namely, in the same temperature and flow rate conditions (surroundings) of the exhaust gas, a difference (changed value) between the pressure loss of the upstream-side detection filter 20 before and after Particulate Matter (PM) is accumulated in the upstream-side detection filter 20 may change in proportion to the change of the amount of Particulate Matter (PM) accumulated in the upstream-side detection filter 20. Therefore, in the same temperature and flow rate conditions (surroundings) of the exhaust gas, by calculating an amount of change of the pressure loss (differential pressure) between the pressures of the upstream side and the downstream side of the upstream-side detection filter 20 from the initial pressure loss (differential pressure) "ΔPa0" to the (current) pressure loss (differential pressure) "ΔPa", it may become possible to calculate the amount of Particulate Matter (PM) accumulated in the upstream-side detection filter 20 based on the amount of change.

Further, as described above, in the process of calculating the amount of Particulate Matter (PM) accumulated in the upstream-side detection filter 20, factors depending on the temperature of the exhaust gas and flow rate of the exhaust gas are included. In order to more accurately calculate the amount of Particulate Matter (PM) accumulated in the upstream-side detection filter 20, it may be required to nondimensionize to remove (cancel) these factors.

To that end, in this embodiment of the present invention, the calculation section 36 periodically detects the pressure loss (differential pressure) "ΔPa" between the pressures of the upstream side and the downstream side of the upstream-side detection filter 20 in the exhaust gas collection line 17 based on the output signal from the pressure sensors 28. Further, the calculation section 36 periodically detects the pressure loss (differential pressure) "ΔPb" between the pressures of the upstream side and the downstream side of the downstream-side detection filter 22 in the exhaust gas collection line 17 based on the output signal from the pressure sensors 34.

Based on the pressure loss (differential pressure) "ΔPb" detected using the output signal from the pressure sensors 34, the calculation section 36 estimates the initial pressure loss (differential pressure) "ΔPb0" in the same conditions (same surroundings) (i.e., in the same temperature condition where the pressure loss (differential pressure) "ΔPb" is detected using the output signal from the pressure sensors 34). Namely, the calculation section 36 estimates the initial pressure loss (differential pressure) "ΔPa0" between the pressures of the upstream side and the downstream side of the upstream-side detection filter 20. Next, based on the estimated initial pressure loss (differential pressure) "ΔPa0" and the pressure loss (differential pressure) "ΔPa" detected using the output signal from the pressure sensors 28, the calculation section 36 calculates the difference (amount of change) between those values (i.e., ΔPa−ΔPa0).

Further, based on the calculated amount of change (ΔPa−ΔPa0) and the estimated initial pressure loss (differential pressure) "ΔPa0", the calculation section 36 calculates a ratio (=(ΔPa−ΔPa0)/ΔPa0). By doing this, the factors depending on the temperature of the exhaust gas and flow rate of the exhaust gas included in the amount of change (ΔPa−ΔPa0) may be removed (cancelled). Then, based on the calculated ratio (32 (ΔPa−ΔPa0)/ΔPa0), by referring to the previously determined relationship between the ratio and the amount of Particulate Matter (PM), the amount of Particulate Matter (PM) accumulated in the upstream-side detection filter 20 may be calculated (determined).

As described above, in this embodiment of the present invention as well, to calculate the amount of Particulate Matter (PM) accumulated in the upstream-side detection filter 20, it is thought that what is necessary is to detect the pressure losses (differences) "ΔPa" and "ΔPb" between the pressures of the upstream side and the downstream side of the upstream-side detection filter 20 and the downstream-side detection filter 22, respectively, which are connected in series in the exhaust gas collection line 17 without detecting any of the temperature of exhaust gas and the flow rate of flowing exhaust gas. Therefore, according to this embodiment of the present invention, by using the pressure losses (differences) "ΔPa" and "ΔPb" detected by the pressure sensors 28 and 34, respectively, without detecting any of the temperature of exhaust gas and the flow rate of flowing exhaust gas, namely without mounting (installing) any of a temperature sensor of the exhaust gas and a flow rate sensor of the exhaust gas, it may become possible to accurately calculate the amount of Particulate Matter (PM) accumulated in the upstream-side detection filter 20. As a result, according to this embodiment of the present invention, it may become possible to reduce the size and cost of the exhaust gas purification apparatus 10 and the fault detection unit 18.

Further, in this embodiment of the present invention, since the upstream-side detection filter 20 and the downstream-side detection filter 22 have substantially the same performance and shapes, unlike the case in the first embodiment of the present invention, it is not necessary to obtain nor store (memorize) the ratio between the initial pressure losses (differences) "ΔPa0" and "ΔPb0"0 of the detection filters 20 and 22, respectively, in order to calculate the amount of Particulate Matter (PM) accumulated in the upstream-side detection filter 20. Therefore, according to this embodiment of the present invention, it may become possible to reduce the size and cost of hardware and software of the exhaust gas purification apparatus 10 in order to calculate the amount of Particulate Matter (PM) accumulated in the upstream-side detection filter 20.

Further, in the second embodiment of the present invention as well, it is not assumed that the performance and the shape of the upstream-side detection filter 106 are the same as those of the downstream-side detection filter 108. However, this third embodiment of the present invention may also be applied to the second embodiment of the present invention as a modification assuming that both upstream-side detection filter 106 and the downstream-side detection filter 108 have substantially the same performance and shape.

Namely, in this modification, the calculation section 122 periodically detects the pressure loss (differential pressure) "ΔPa" between the pressures of the upstream side and the downstream side of the upstream-side detection filter 106 in the exhaust gas collection line 102 based on the output signal from the pressure sensors 114. Further, the calculation section 122 periodically detects the pressure loss (differential pressure) "ΔPb" between the pressures of the upstream side and the downstream side of the downstream-side detection filter 108 in the exhaust gas collection line 102 based on the output signal from the pressure sensors 120.

Based on the pressure loss (differential pressure) "ΔPb" detected using the output signal from the pressure sensors 120, the calculation section 122 estimates the initial pressure loss (differential pressure) "ΔPb0" in the same conditions (same surroundings) (i.e., in the same temperature condition where the pressure loss (differential pressure) "ΔPb" is detected using the output signal from the pressure sensors 120). Namely, the calculation section 122 estimates the initial pressure loss (differential pressure) "ΔPa0" between the pressures of the upstream side and the downstream side of the upstream-side detection filter 106. Next, based on the estimated initial pressure loss (differential pressure) "ΔPa0" and the pressure loss (differential pressure) "ΔPa" detected using the output signal from the pressure sensors 114, the calculation section 122 calculates the difference (amount of change) between those values (i.e., ΔPa−ΔPa0).

Further, based on the calculated amount of change (ΔPa−ΔPa0) and the estimated initial pressure loss (differential pressure) "ΔPa0", the calculation section 122 calculates a ratio (32 (ΔPa−ΔPa0)/ΔPa0). By doing this, the factors depending on the temperature of the exhaust gas and flow rate of the exhaust gas included in the amount of change (ΔPa−ΔPa0) may be removed (cancelled). Then, based on the calculated ratio (=(ΔPa−ΔPa0)/ΔPa0), by referring to the previously determined relationship between the ratio and the amount of Particulate Matter (PM), the amount of Particulate Matter (PM) accumulated in the upstream-side detection filter 106 may be calculated (determined).

As described above, in this modification as well, to calculate the amount of Particulate Matter (PM) accumulated in the upstream-side detection filter 106, it is thought that what is necessary is to detect the pressure losses (differences) "ΔPa" and "ΔPb" between the pressures of the upstream side and the downstream side of the upstream-side detection filter 106 and the downstream-side detection filter 108, respectively, which are connected in series in the exhaust gas collection line 102 without detecting any of the temperature of exhaust gas and the flow rate of flowing exhaust gas. Therefore, according to this modification, by using the pressure losses (differences) "ΔPa" and "ΔPb" detected by the pressure sensors 114 and 120, respectively, without detecting any of the temperature of exhaust gas and the flow rate of flowing exhaust gas, namely without mounting (installing) any of a temperature sensor of the exhaust gas and a flow rate sensor of the exhaust gas, it may become possible to accurately calculate the amount of Particulate Matter (PM) accumulated in the upstream-side detection filter 106. As a result, according to this embodiment of the present invention, it may become possible to reduce the size and cost of the exhaust gas purification apparatus 100 and the measurement unit 104.

Further, in this embodiment of the present invention, since the upstream-side detection filter 106 and the downstream-side detection filter 108 have substantially the same performance and shape, unlike the case in the second embodiment of the present invention, it is not necessary to obtain nor store (memorize) the ratio between the initial pressure losses (differences) "ΔPa0" and "ΔPb0" of the detection filters 106 and 108, respectively, in order to calculate the amount of Particulate Matter (PM) accumulated in the upstream-side detection filter 106. Therefore, according to this embodiment of the present invention, it may become possible to reduce the size and cost of hardware and software of the exhaust gas purification apparatus 100 in order to calculate the amount of Particulate Matter (PM) accumulated in the upstream-side detection filter 106.

As described above, preferred embodiments of the present invention and modifications thereof are described. However, the present invention is not limited to the embodiments and the modifications thereof described above, and various modifications, transformations, alterations, exchanges, and the like may be made without departing from the scope and spirit of the present invention.

For example, in the above embodiments, the pressure losses (differences) of the two detection filters 20 and 22 in the first embodiment (detection filters 106 and 108 in the second embodiment) are detected using the two pressure sensors 28 and 34 in the first embodiment (pressure sensors 114 and 120 in the second embodiment). However, each of a pressure applied to the upstream side of the upstream-side detection filter 20 (106), a pressure applied to the downstream side of the upstream-side detection filter 20 (106) (i.e., the upstream side of the downstream-side detection filter 22 (108)), and a pressure applied to the downstream side of the downstream-side detection filter 22 (108) may be separately detected by providing three pressure sensors. Then, by calculating from the detected pressures, the pressure losses (differences) of the two detection filters 20 and 22 (106 and 108) may be obtained.

Further, in the above second embodiment, as shown in FIG. 5, the exhaust gas collection line 102 is connected in parallel with the main exhaust pipe 14 so as to bypass the Diesel Particulate Filter (DPF) 16. Namely, the upstream end and the downstream end of the exhaust gas collection line 102 are connected to the main exhaust pipe 14a and the main exhaust pipe 14b, respectively. However, the present invention is not limited to this connecting method. For example, the downstream end of the exhaust gas collection line 102 may be connected to a pump so as to introduce exhaust gas into the exhaust gas collection line 102. Otherwise, for example, the downstream end of the exhaust gas collection line 102 may be connected to the main exhaust pipe 14a on the upstream side of the Diesel Particulate Filter (DPF) 16 or directly connected to atmosphere.

Figure 7:
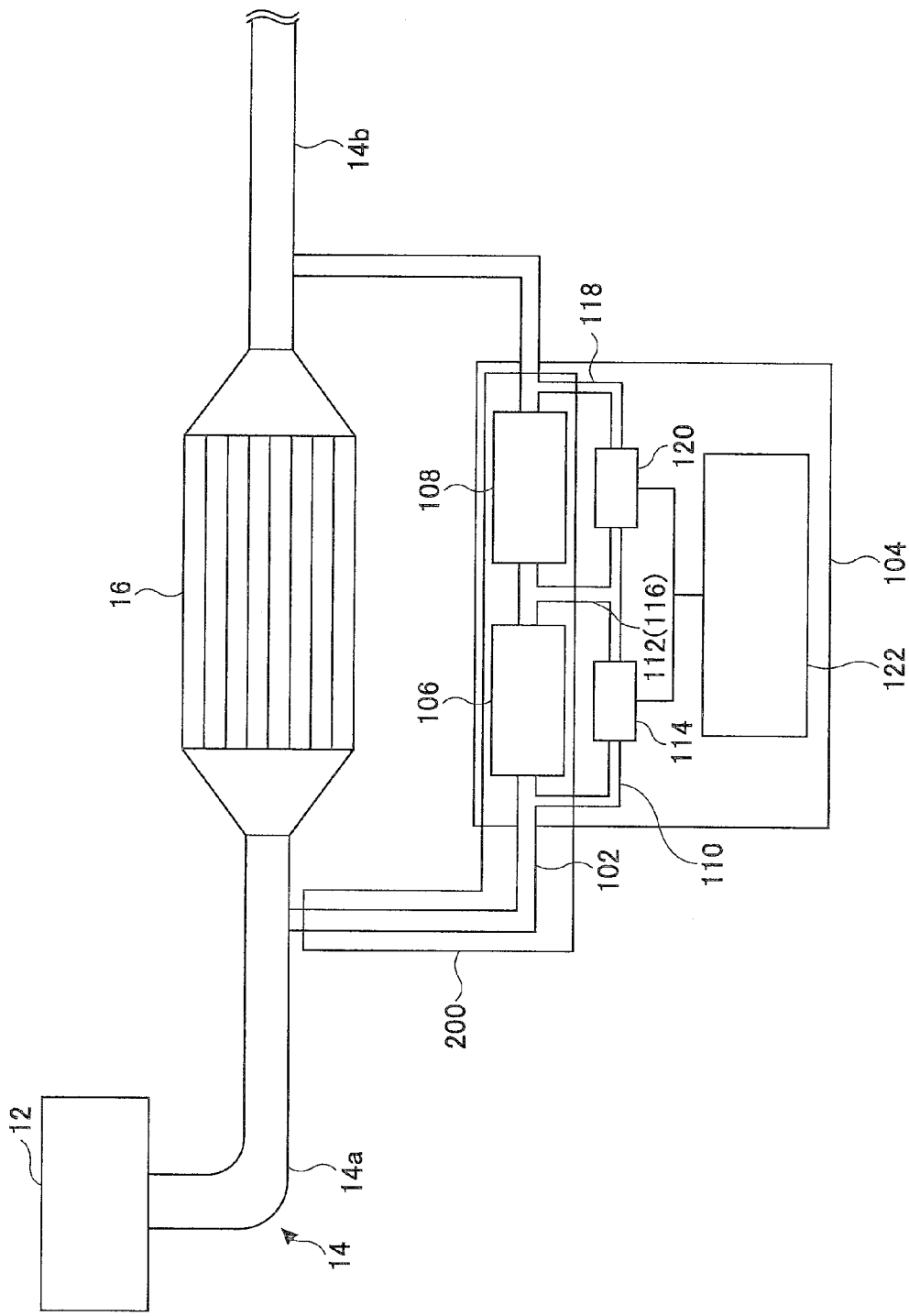
FIG. 7 is a schematic drawing showing a configuration of a construction of a modified exhaust gas purification apparatus according to the second embodiment of the present invention.

Further, in the second embodiment of the present invention, there is no heat retaining means provided for keeping the temperature of exhaust gas throughout the exhaust gas collection line 102 and the detection filters 106 and 108 at a constant temperature. However, as shown in FIG. 7, a heat retaining means 200 may be added for that purpose. In this case, typically, the heat retaining means 200 may be a heater such as an electrically-heated wire. In this modification where the heat retaining means 200 is provided, temperature change throughout the exhaust gas collection line 102 and the detection filters 106 and 108 may be better-controlled, thereby enabling preventing dew condensation in the exhaust gas collection line 102 and the detection filters 106 and 108 and making it possible to keep the initial pressure losses (differences) "ΔPa0" and "ΔPb0" of the detection filters 106 and 108 at constant values.

Figure 8:
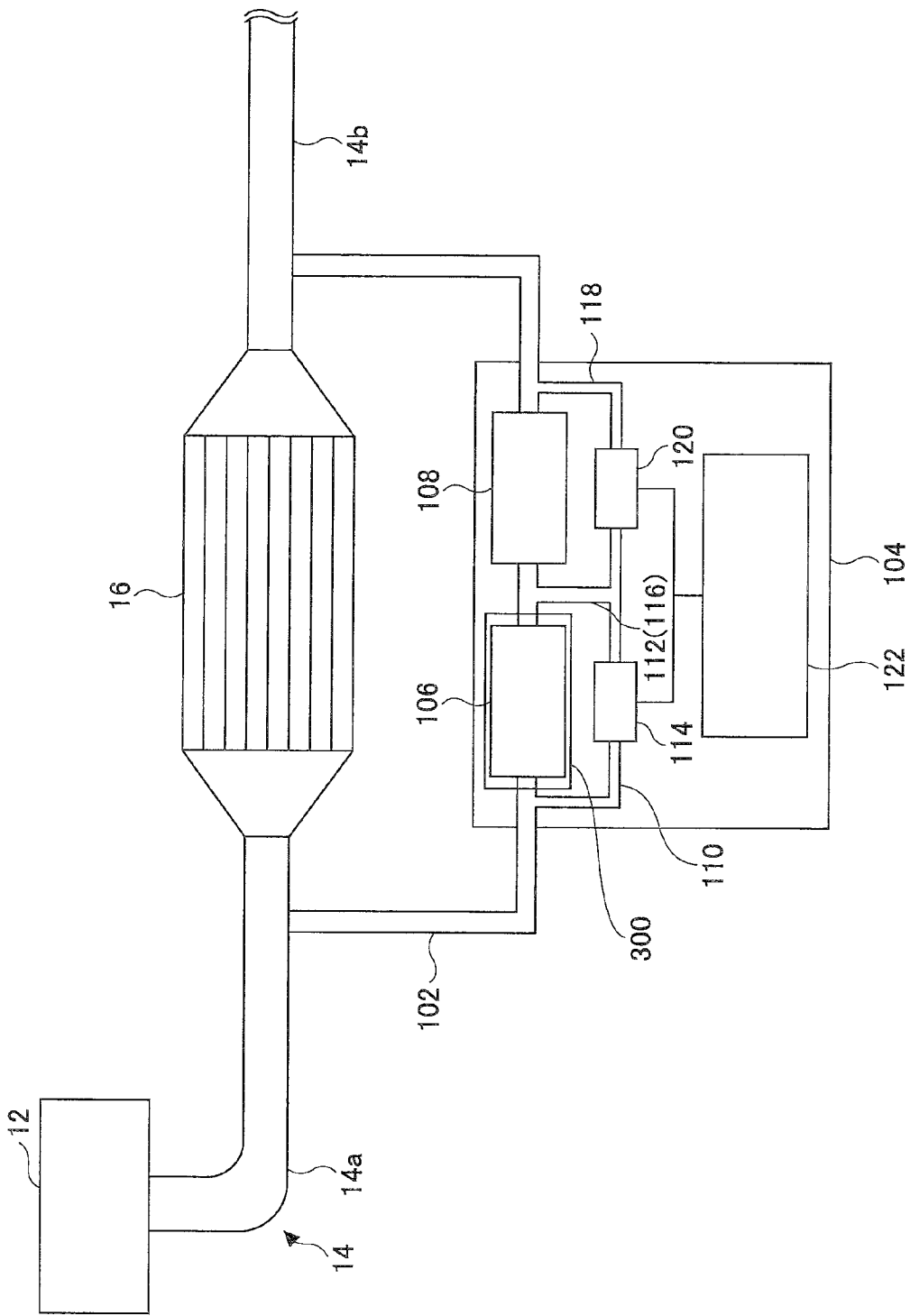
FIG. 8 is a schematic drawing showing a configuration of a construction of another modified exhaust gas purification apparatus according to the second embodiment of the present invention.

Further, in the second embodiment of the present invention, there is no Particulate Matter (PM) removal means (regeneration means) for burning and oxidizing the Particulate Matter (PM) accumulated in the upstream-side detection filter 106 to remove the Particulate Matter (PM) from the upstream-side detection filter 106. However, as shown in FIG. 8, a regeneration means 300 may be added for that purpose. In this case, typically, the regeneration means 300 may be, for example, a heater such as an electrically-heated wire, a burner or the like. Further, for example, the regeneration means 300 may be operated in synchronization with the regeneration timing of the Diesel Particulate Filter (DPF) 16. In this modification where the regeneration means 300 is provided, the Particulate Matter (PM) accumulated in the upstream-side detection filter 106 may be burned and oxidized to regenerate the upstream-side detection filter 106, thereby enabling calculating (estimating) the amount of Particulate Matter (PM) accumulated in the Diesel Particulate Filter (DPF) 16 more accurately.

Further, there may be a case where the Particulate Matter (PM) accumulated in the upstream-side detection filter 106 leaks to the downstream side of the upstream-side detection filter 106. Therefore, the Particulate Matter (PM) removal means (regeneration means) may also be added for the downstream-side detection filter 108 so as to burn and oxidize the Particulate Matter (PM) accumulated in the downstream-side detection filter 108 to regenerate the downstream-side detection filter 108.

In this description, the particulate matter sensor is referred to as the detection unit or the measurement unit; the upstream-side detection filter and the downstream-side detection filter are referred to as the first detection filter and the second detection filter, respectively; the pressure loss (difference) between the upstream side and the down stream side of the upstream-side detection filter is referred to as the first differential pressure and a unit for detecting the first differential pressure is referred to as the first differential pressure detection unit; and the pressure loss (difference) between the upstream side and the down stream side of the downstream-side detection filter is referred to as the second differential pressure and a unit for detecting the second differential pressure is referred to as the second differential pressure detection unit.

What is claimed is:

1. A particulate matter sensor comprising:
    a first detection filter provided in an exhaust gas flow passage and capable of collecting particle matter;
    a second detection filter provided on a downstream side of the first detection filter in the exhaust gas flow passage and capable of collecting the particle matter;
    a first differential pressure detection unit configured to detect a first differential pressure between pressures of an upstream side and the downstream side of the first detection filter;
    a second differential pressure detection unit configured to detect a second differential pressure between pressures of an upstream side and a downstream side of the second detection filter; and
    a particle matter amount detection unit configured to detect an amount of particle matter based on a detection result of the first differential pressure detection unit and a detection result of the second differential pressure detection unit, wherein
    the particle matter amount detection unit comprises:
        a first differential pressure initial value estimation unit configured to, based on an initial ratio between the first differential pressure and the second differential pressure and based on the second differential pressure detected by the second differential pressure detection unit, estimate an initial value of the first differential pressure in same conditions where the second differential pressure is detected by the second differential pressure detection unit; and
        a ratio calculation unit configured to calculate a ratio between the initial value of the first differential pressure estimated by the first differential pressure initial value estimation unit and the first differential pressure detected by the first differential pressure detection unit, wherein
    the particle matter amount detection unit is configured to detect the amount of particle matter based on the ratio calculated by the ratio calculation unit.

2. The particulate matter sensor according to claim 1, wherein
    the first detection filter and the second detection filter are provided at substantially a same temperature range in the exhaust gas flow passage.

3. The particulate matter sensor according to claim 1, further comprising:
    a heat retaining unit configured to keep temperatures of the first detection filter and the second detection filter at substantially a same temperature.

4. The particulate matter sensor according to claim 1, further comprising:
    a particle matter removal unit configured to remove particle matter accumulated in the first detection filter or the second detection filter.

5. The particulate matter sensor according to claim 4, wherein
    the particle matter removal unit comprises at least one of a heater and a burner configured to burn and remove the accumulated particle matter.

6. The particulate matter sensor according to claim 1, wherein
    the first detection filter and the second detection filter have substantially a same performance with each other,
    the particle matter amount detection unit comprises:
        a difference calculation unit configured to calculate a difference between the first differential pressure detected by the first differential pressure detection unit and the second differential pressure detected by the second differential pressure detection unit, wherein
    the particle matter amount detection unit is configured to detect the amount of particle matter based on the difference calculated by the difference calculation unit.

7. The particulate matter sensor according to claim 6, wherein
    the first detection filter and the second detection filter comprise a single formed body.

8. An exhaust gas purification apparatus comprising:
    a diesel particulate filter capable of collecting particle matter in exhaust gas exhausted from an internal combustion engine and passing through an exhaust pipe;

the particulate matter sensor according to claim 1 comprising a particle matter accumulation amount calculation unit configured to calculate an amount of particle matter accumulated in the diesel particulate filter based on the amount of particle matter detected by the particulate matter sensor; and an upstream-side exhaust gas introduction unit configured to introduce a part of the exhaust gas from the exhaust pipe on an upstream side of the diesel particulate filter into the particulate matter sensor.

9. An exhaust gas purification apparatus comprising:

a diesel particulate filter capable of collecting particle matter in exhaust gas exhausted from an internal combustion engine and passing through an exhaust pipe;

the particulate matter sensor according to claim 2 comprising a particle matter accumulation amount calculation unit configured to calculate an amount of particle matter accumulated in the diesel particulate filter based on the amount of particle matter detected by the particulate matter sensor; and an upstream-side exhaust gas introduction unit configured to introduce a part of the exhaust gas from the exhaust pipe on an upstream side of the diesel particulate filter into the particulate matter sensor.

10. An exhaust gas purification apparatus comprising:

a diesel particulate filter capable of collecting particle matter in exhaust gas exhausted from an internal combustion engine and passing through an exhaust pipe;

the particulate matter sensor according to claim 3 comprising a particle matter accumulation amount calculation unit configured to calculate an amount of particle matter accumulated in the diesel particulate filter based on the amount of particle matter detected by the particulate matter sensor; and an upstream-side exhaust gas introduction unit configured to introduce a part of the exhaust gas from the exhaust pipe on an upstream side of the diesel particulate filter into the particulate matter sensor.

11. An exhaust gas purification apparatus comprising:

a diesel particulate filter capable of collecting particle matter in exhaust gas exhausted from an internal combustion engine and passing through an exhaust pipe;

the particulate matter sensor according to claim 4 comprising a particle matter accumulation amount calculation unit configured to calculate an amount of particle matter accumulated in the diesel particulate filter based on the amount of particle matter detected by the particulate matter sensor; and an upstream-side exhaust gas introduction unit configured to introduce a part of the exhaust gas from the exhaust pipe on an upstream side of the diesel particulate filter into the particulate matter sensor.

12. An exhaust gas purification apparatus comprising:

a diesel particulate filter capable of collecting particle matter in exhaust gas exhausted from an internal combustion engine and passing through an exhaust pipe;

the particulate matter sensor according to claim 5 comprising a particle matter accumulation amount calculation unit configured to calculate an amount of particle matter accumulated in the diesel particulate filter based on the amount of particle matter detected by the particulate matter sensor; and an upstream-side exhaust gas introduction unit configured to introduce a part of the exhaust gas from the exhaust pipe on an upstream side of the diesel particulate filter into the particulate matter sensor.

13. An exhaust gas purification apparatus comprising:

a diesel particulate filter capable of collecting particle matter in exhaust gas exhausted from an internal combustion engine and passing through an exhaust pipe;

the particulate matter sensor according to claim 6 comprising a particle matter accumulation amount calculation unit configured to calculate an amount of particle matter accumulated in the diesel particulate filter based on the amount of particle matter detected by the particulate matter sensor; and an upstream-side exhaust gas introduction unit configured to introduce a part of the exhaust gas from the exhaust pipe on an upstream side of the diesel particulate filter into the particulate matter sensor.

14. An exhaust gas purification apparatus comprising:

a diesel particulate filter capable of collecting particle matter in exhaust gas exhausted from an internal combustion engine and passing through an exhaust pipe;

the particulate matter sensor according to claim 7 comprising a particle matter accumulation amount calculation unit configured to calculate an amount of particle matter accumulated in the diesel particulate filter based on the amount of particle matter detected by the particulate matter sensor; and an upstream-side exhaust gas introduction unit configured to introduce a part of the exhaust gas from the exhaust pipe on an upstream side of the diesel particulate filter into the particulate matter sensor.

15. An exhaust gas purification apparatus comprising:

a diesel particulate filter capable of collecting particle matter in exhaust gas exhausted from an internal combustion engine and passing through an exhaust pipe;

the particulate matter sensor according to claim 1 comprising a filter fault diagnosis unit configured to diagnose whether the diesel particulate filter is in a faulty state based on the amount of particle matter detected by the particulate matter sensor; and a downstream-side exhaust gas introduction unit configured to introduce a part of the exhaust gas from the exhaust pipe on a downstream side of the diesel particulate filter into the particulate matter sensor.

16. An exhaust gas purification apparatus comprising:

a diesel particulate filter capable of collecting particle matter in exhaust gas exhausted from an internal combustion engine and passing through an exhaust pipe;

the particulate matter sensor according to claim 2 comprising a filter fault diagnosis unit configured to diagnose whether the diesel particulate filter is in a faulty state based on the amount of particle matter detected by the particulate matter sensor; and a downstream-side exhaust gas introduction unit configured to introduce a part of the exhaust gas from the exhaust pipe on a downstream side of the diesel particulate filter into the particulate matter sensor.

17. An exhaust gas purification apparatus comprising:

a diesel particulate filter capable of collecting particle matter in exhaust gas exhausted from an internal combustion engine and passing through an exhaust pipe;

the particulate matter sensor according to claim 3 comprising a filter fault diagnosis unit configured to diagnose whether the diesel particulate filter is in a faulty state based on the amount of particle matter detected by the particulate matter sensor; and a downstream-side exhaust gas introduction unit configured to introduce a part of the exhaust gas from the exhaust pipe on a downstream side of the diesel particulate filter into the particulate matter sensor.

18. An exhaust gas purification apparatus comprising:
a diesel particulate filter capable of collecting particle matter in exhaust gas exhausted from an internal combustion engine and passing through an exhaust pipe;
the particulate matter sensor according to claim 4 comprising a filter fault diagnosis unit configured to diagnose whether the diesel particulate filter is in a faulty state based on the amount of particle matter detected by the particulate matter sensor; and
a downstream-side exhaust gas introduction unit configured to introduce a part of the exhaust gas from the exhaust pipe on a downstream side of the diesel particulate filter into the particulate matter sensor.

19. An exhaust gas purification apparatus comprising:
a diesel particulate filter capable of collecting particle matter in exhaust gas exhausted from an internal combustion engine and passing through an exhaust pipe;
the particulate matter sensor according to claim 5 comprising a filter fault diagnosis unit configured to diagnose whether the diesel particulate filter is in a faulty state based on the amount of particle matter detected by the particulate matter sensor; and
a downstream-side exhaust gas introduction unit configured to introduce a part of the exhaust gas from the exhaust pipe on a downstream side of the diesel particulate filter into the particulate matter sensor.

20. An exhaust gas purification apparatus comprising:
a diesel particulate filter capable of collecting particle matter in exhaust gas exhausted from an internal combustion engine and passing through an exhaust pipe;
the particulate matter sensor according to claim 6 comprising a filter fault diagnosis unit configured to diagnose whether the diesel particulate filter is in a faulty state based on the amount of particle matter detected by the particulate matter sensor; and
a downstream-side exhaust gas introduction unit configured to introduce a part of the exhaust gas from the exhaust pipe on a downstream side of the diesel particulate filter into the particulate matter sensor.

21. An exhaust gas purification apparatus comprising:
a diesel particulate filter capable of collecting particle matter in exhaust gas exhausted from an internal combustion engine and passing through an exhaust pipe;
the particulate matter sensor according to claim 7 comprising a filter fault diagnosis unit configured to diagnose whether the diesel particulate filter is in a faulty state based on the amount of particle matter detected by the particulate matter sensor; and
a downstream-side exhaust gas introduction unit configured to introduce a part of the exhaust gas from the exhaust pipe on a downstream side of the diesel particulate filter into the particulate matter sensor.

* * * * *